United States Patent
Natan et al.

(10) Patent No.: US 9,726,609 B2
(45) Date of Patent: Aug. 8, 2017

(54) WAVELENGTH SELECTIVE SERS NANOTAGS

(71) Applicant: SICPA HOLDING SA, Albuquerque, NE (US)

(72) Inventors: Michael J. Natan, Los Altos, CA (US); Richard D. Freeman, Mountain View, CA (US); William E. Doering, Santa Clara, CA (US); Marcelo E. Piotti, Freemont, CA (US)

(73) Assignee: SICPA HOLDING SA, Prilly (CH)

( * ) Notice: Subject to any disclaimer, the term of this patent is extended or adjusted under 35 U.S.C. 154(b) by 0 days.

(21) Appl. No.: 14/594,905

(22) Filed: Jan. 12, 2015

(65) Prior Publication Data

US 2015/0160136 A1    Jun. 11, 2015

Related U.S. Application Data

(63) Continuation of application No. 13/635,559, filed as application No. PCT/US2011/029395 on Mar. 22, 2011, now abandoned.

(Continued)

(51) Int. Cl.
*F21V 9/00*    (2015.01)
*G02B 5/02*    (2006.01)
(Continued)

(52) U.S. Cl.
CPC ............ *G01N 21/658* (2013.01); *B82Y 30/00* (2013.01); *H01S 3/30* (2013.01); *B82Y 20/00* (2013.01);
(Continued)

(58) Field of Classification Search
USPC .................... 205/112, 150; 252/301.16, 582; 356/301, 71, 72; 427/162, 212, 435, 180;
(Continued)

(56) References Cited

U.S. PATENT DOCUMENTS

| 6,514,767 B1 | 2/2003 | Natan |
|---|---|---|
| 6,861,263 B2 | 3/2005 | Natan |

(Continued)

FOREIGN PATENT DOCUMENTS

| JP | 2009-249249 | 10/2009 |
|---|---|---|
| JP | 2009249249 | * 10/2009 |

OTHER PUBLICATIONS

Shawn P. Mulvaney, Michael D. Musick, Christine D. Keating, and Michael J. Natan, Glass-Coated, Analyte-Tagged Nanoparticles: A New Tagging System Based on Detection with Surface-Enhanced Raman Scattering, Langmuir 2003, 19, 4784-4790.*

(Continued)

*Primary Examiner* — Bijan Ahvazi
(74) *Attorney, Agent, or Firm* — Swanson & Bratschun, L.L.C.

(57) ABSTRACT

Materials and objects tagged with wavelength selective particles such as SERS nanotags modified for wavelength selectivity. As used herein, a wavelength selective particle is one which cannot be effectively excited or interrogated at one or more wavelengths where a reporter molecule associated with the particle would normally produce a spectrum. Also disclosed are methods of manufacturing wavelength selective particles and methods of tagging materials or objects with wavelength selective particles.

13 Claims, 9 Drawing Sheets

Related U.S. Application Data

(60) Provisional application No. 61/316,284, filed on Mar. 22, 2010.

(51) Int. Cl.

| | |
|---|---|
| *G02C 7/10* | (2006.01) |
| *G02F 1/361* | (2006.01) |
| *G03B 11/00* | (2006.01) |
| *G01N 21/65* | (2006.01) |
| *B82Y 30/00* | (2011.01) |
| *H01S 3/30* | (2006.01) |
| *G06K 9/74* | (2006.01) |
| *G01N 21/00* | (2006.01) |
| *G01J 3/44* | (2006.01) |
| *G02F 1/35* | (2006.01) |
| *G02F 2/02* | (2006.01) |
| *B82Y 20/00* | (2011.01) |

(52) U.S. Cl.
CPC ... *G01N 2201/06113* (2013.01); *Y10S 977/81* (2013.01); *Y10S 977/834* (2013.01)

(58) Field of Classification Search
USPC .............. 428/323, 403; 435/287.2; 436/518; 977/700, 902, 810, 834; 359/327
See application file for complete search history.

(56) References Cited

U.S. PATENT DOCUMENTS

| | | | |
|---|---|---|---|
| 7,192,778 B2 | 3/2007 | Natan | |
| 7,443,489 B2 | 10/2008 | Natan | |
| 2006/0054506 A1* | 3/2006 | Natan | B22F 205/112 205/112 |
| 2007/0155021 A1 | 7/2007 | Zhang | |
| 2007/0165209 A1* | 7/2007 | Natan | G01J 3/44 356/71 |
| 2008/0266555 A1 | 10/2008 | Murphy | |
| 2009/0140206 A1 | 6/2009 | Nie | |

OTHER PUBLICATIONS

Yuanzhe Piao, Andrew Burns, Jaeyun Kim, Ulrich Wiesner, and Taeghwan Hyeon,Designed Fabrication of Silica-Based Nanostructured Particle Systems for Nanomedicine Applications,Adv. Funct. Mater. 2008, 18, 3745-3758. 2008 WILEY-VCH Verlag GmbH & Co. KGaA, Weinheim.*

Xin Li, Jun Qian and Sailing He, Impact of the self-assembly of multilayer polyelectrolyte functionalized gold nanorods and its application to biosensing, Nanotechnology 19 (2008) 355501. © 2008 IOP 1 Publishing Ltd Printed in the UK.*

Mulvaney, et al., (2003) Langmuir 19: 4784-4790, "Analyte-Tagged Nanoparticles: A New Tagging System Based on Detection with Surface-Enhanced Raman Scattering".

Piao, et al. (2008) Adv. Funct. Mater 18: 3745-3758, "Designed Fabrication of Silica-Based Nanostructured Particle Systems for Nanomedicine Applications".

Li, et al. (2008) Nanotechnology 19: 355501 © 2008 IOP 1 Publishing Ltd Printed in the UK, "Impact of the self-assemtly of multilayer polyelectrolyte functionalized gold nanorods and its application to biosensing".

International Preliminary Report on Patentability for International Application No. PCT/US2011/029395 mailed Oct. 4, 2012.

International Search Report and Written Opinion for International Application No. PCT/US2011/029395, mailed on May 23, 2011.

* cited by examiner

WAVELENGTH SELECTIVE SERS NANOTAGS

RELATED APPLICATIONS

This application is a continuation of U.S. patent application Ser. No. 13/635,559 filed Sep. 17, 2012, entitled "Wavelength Selective SERS Nanotags," which claims priority under 35 USC §371 to PCT Application Serial No. PCT/US2011/02939, filed Mar. 22, 2011, entitled "Wavelength Selective SERS Nanotags," which claims priority to U.S. Provisional Application No. 61/316,284, filed Mar. 22, 2010, entitled "Wavelength Selective SERS Nanotags," which are each incorporated herein in their entirety by reference.

BACKGROUND

SERS nanotags have proved useful for marking objects for identification and tracking. SERS nanotags are nanoparticulate optical detection tags which function through surface enhanced Raman scattering (SERS). SERS is a laser-based optical spectroscopy that, for molecules or other materials, generates a fingerprint-like vibrational spectrum with features that are much narrower than typical fluorescence.

Typically, a SERS active molecule associated with a tag is excited by laser light at a specific excitation wavelength. Many SERS active molecules can be excited at several alternative wavelengths with each wavelength causing the emission of a characteristic SERS spectrum. In some marking uses the ability of a known SERS nanotag to be interrogated at multiple suitable interrogation wavelengths is an advantage. In other implementations, such as covert item marking, the ability to excite a SERS nanotag at multiple wavelengths is potentially a disadvantage, since this makes covert tags easier to detect by third parties. It is difficult however to manufacture a SERS nanotag that can be interrogated at a limited number of otherwise suitable wavelengths with conventional SERS reporter molecules.

The embodiments disclosed herein are directed toward overcoming these or other problems associated with known surface enhanced spectroscopy particles.

SUMMARY OF THE EMBODIMENTS

Selected embodiments include wavelength selective particles such as SERS nanotags modified as described. As used herein, a wavelength selective particle is one which cannot be effectively excited or interrogated at one or more wavelengths where a reporter molecule associated with the particle would normally produce a SERS spectrum. For example, a wavelength selective SERS nanotag might be SERS active when using a 1064 nm excitation wavelength but inactive at 785 nm, where activity at 785 nm would otherwise be expected based upon the reporter molecule present in the SERS nanotag or the plasmonic properties of the metal nanoparticle.

One embodiment of SERS nanotag which is wavelength selective includes a SERS enhancing core and a SERS active reporter molecule associated with the core. The wavelength selective SERS tag also includes an encapsulant surrounding the core/reporter association. Wavelength selectivity may be imparted by a blocking material associated with the encapsulant which fully or partially blocks the passage of light energy at a specific wavelength to the reporter molecule and plasmonic particle. Alternatively, the blocking material could wholly or partially block the radiation of light energy at a selected wavelength from the reporter molecule or plasmonic particle.

The blocking material could be a nanorod, for example, a gold nanorod associated with the encapsulant. Alternatively, the blocking material could be a molecule of any type which serves to selectively block a relevant wavelength. For example, the blocking material could be an organic or inorganic dye or a quantum dot particle. Alternatively, the blocking material could be a metal oxide, metal sulfide, metal nitride, or other similar material.

In embodiments where the blocking material is a nanorod, the nanorod may be electrostaticly associated with the encapsulant. For example, the nanorod may be coated with a charged polymer and the SERS nanotag coated with an oppositely charged polymer. Alternatively, the nanorod may be covalent attached to the encapsulant.

In embodiments where the blocking material is a molecule such as a dye, an increased quantity of blocking material may be associated with the encapsulant by forming the encapsulant as a porous or mesoporous surface.

An alternative embodiment includes a SERS nanotag as described above with a masking material associated with the encapsulant. A masking material will wholly or partially mask light energy emitted at a given wavelength by the reporter molecule. In a masking embodiment, the reporter associated with the SERS nanotag will still emit a Raman spectrum when excited but the emission is masked or otherwise made undetectable. For example, a fluorescent molecule associated with the SERS nanotag may be selected to fluoresce at a particular wavelength, thus masking the SERS spectrum at that wavelength.

Alternative embodiments include methods of manufacturing a wavelength selective SERS nanotag as described above. Alternative methods also include using a wavelength selective SERS nanotag to mark or tag an item, substance, document or article, such that the tag may be detected at fewer interrogation frequencies than would be expected based upon the nature of the reporter molecule used with the SERS nanotag.

DETAILED DESCRIPTION

Figure 1:
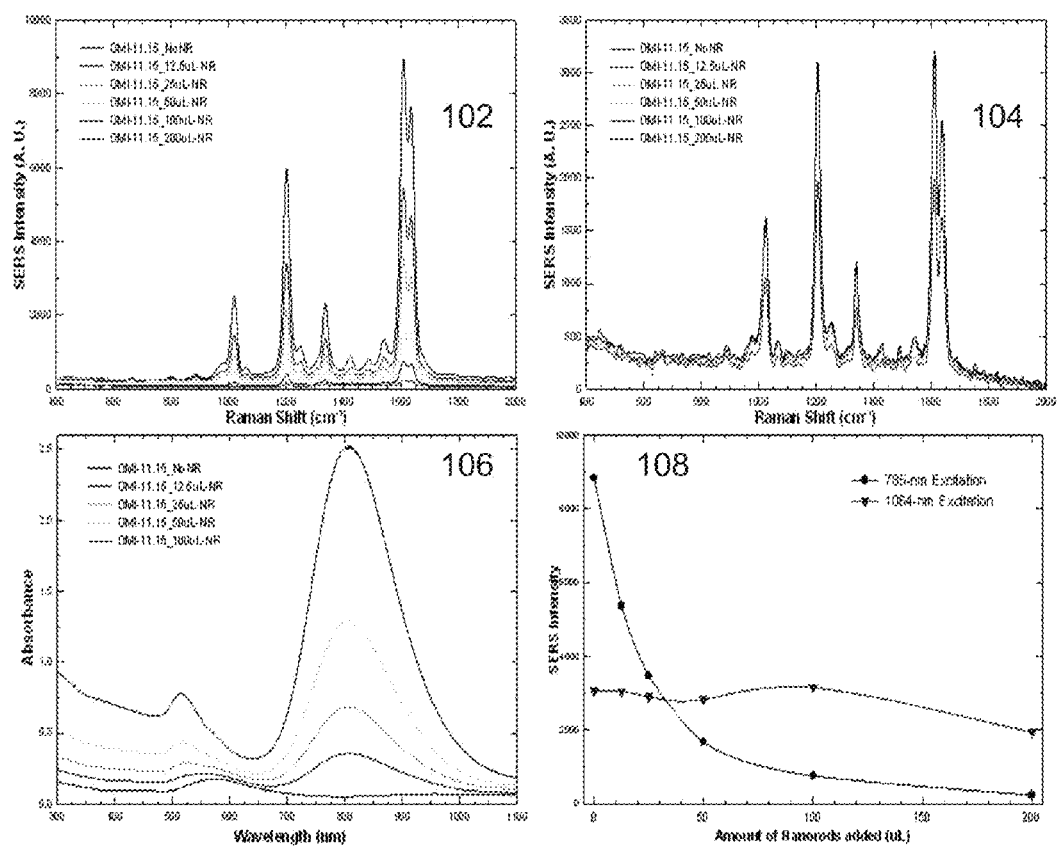
FIG. 1 is a graphic representation of the SERS activity and absorbance of the mixture of SERS nanotags and Au nanorods of Example 1.

The embodiments disclosed herein relate to particles that are spectroscopically active. In particular, the disclosed particles and methods are surface-enhanced spectroscopy (SES) active. Representative SES techniques include but are not limited to SERS, SERRS and others. Surface enhancement in various other spectroscopy methods or systems has been observed. The most widely studied have been surface-enhanced Raman scattering and surface-enhanced fluorescence (SEF). But a variety of other surface enhanced phenomena have been observed including surface-enhanced hyper Raman scattering (SEHRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells. As used throughout this disclosure SES includes the above listed and any related or similar spectroscopic technique.

Many of the examples herein are described with respect to SERS. It must be noted however that the methods, compositions and particles disclosed herein are equally applicable to SERRS, SEHRS, SEF, SEHRRS, SHG, SEIRA, SPASERS, or other surface enhanced or plasmon enhanced SES technique.

In general, taggants are materials, substances, molecules, ions, polymers, nanoparticles, microparticles, or other matter, incorporated into, onto or otherwise associated with objects for the purposes of identification or quantitation. More specifically, taggants are used in activities and products including but not limited to detection, analysis, and/or quantification measurements related to brand security, brand protection, trademark protection, product security, product identification, brand diversion, bar-coding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, and standoff detection/identification.

Taggants can be added to all forms of matter, including but not limited to solids, liquids, gases, gels, foams, semi-solids, glasses, plasmas, liquid crystals, amorphous and magnetically-ordered solids, superconductors, superfluids, Bose-Einstein condensates, and supersolids.

Many known methods of detecting taggants utilize one of several spectroscopic techniques, for example a surface-enhanced spectroscopy (SES) techniques such as SERS or SERRS. Broadly speaking, suitable materials fall in two categories: nano/microscale and macroscopic. For example, certain sizes and shapes of Ag and Au nanoparticles, and aggregates thereof, are known to support SERS. Likewise, a large variety of macroscopic SERS substrates have been described in the literature, including electrodes, evaporated films, Langmuir-Blodgett films, 2-dimensional planar arrays, and so forth.

Known prior art tagging methods which utilize SERS-active tags typically include a reporter molecule or dye with known SERS-active characteristics. For example, a known SERS-active chemical can be added as a dye to mark fuel and a subsequent SERS spectrum obtained when the SERS-active dye is associated with a SERS-active metal particle or substrate. Only a limited number of SERS active chemicals are known.

Many of the embodiments disclosed herein feature the use of a surface-enhanced spectroscopy (SES) active taggant. The most widely studied have been surface-enhanced Raman scattering and surface-enhanced fluorescence (SEF). But a variety of other surface enhanced phenomena have been observed including surface-enhanced hyper Raman scattering (SEHRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells. As used throughout this disclosure SES includes the above listed and any related or similar spectroscopic technique.

Many of the examples herein are described with respect to SERS. It must be noted however that the methods, compositions and particles disclosed herein are equally applicable to SERRS, SEHRS, SEF, SEHRRS, SHG, SEIRA, SPASERS, or other surface enhanced or plasmon enhanced SES technique.

Surface enhanced Raman scattering (SERS)-active particles are useful in a variety of applications. One interesting application is anti-counterfeiting, and more specifically to verify the authenticity, source, age, and/or distribution path of banknotes, tax stamps, banderols, passports, identification cards, driver's licenses, work permits, fiduciary documents, stock and bond certificates, and other valuable documents that contain ink. Likewise, SERS-active particles can be used for similar purposes to mark or tag a variety of other materials that contain print or lettering composed of ink or lacquer, including but not limited to software, machine parts such as airplane parts or automobile parts, instrumentation, pharmaceutical and diagnostic products, medical devices, luxury goods, fast-moving consumer goods, CD's, DVD's and other electronic storage components, and so forth. Moreover, any ink- or lacquer-containing packaging for any type of product is a viable location for introduction of SERS-active particles for anti-counterfeiting, or authentication purposes. Additional closely related applications for SERS-active particles include: brand security, brand protection, trademark protection, product security, product identification, brand diversion, barcoding, grey market remediation, friend-or-foe analysis, product life cycle analysis, counterfeiting, forensic analysis of authenticity, biometrics, document tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, object tracking, standoff detection, and/or standoff identification. In addition, SERS-active particles can be used for combinations of these applications, including but not limited to a combination of authentication and sell-by-date tracking. Collectively, these applications are referred to as Industrial Security.

One non-exclusive and non-limiting type of tag which is described herein and which may be modified according to the disclosed methods and with the disclosed materials is a SERS nanotag also referred to as a SERS tag. SERS nanotags are nanoparticulate optical detection tags which function through surface enhanced Raman scattering (SERS). SERS is a laser-based optical spectroscopy that, for molecules, generates a fingerprint-like vibrational spectrum with features that are much narrower than typical fluorescence.

A typical SERS nanotag includes a metal nanoparticle core and a $SiO_2$ (glass) or other silicon containing encapsulant. Other materials including but not limited to various types of polymers may also be used as an encapsulant or shell. Details concerning the use, manufacture and characteristics of a typical SERS nanotag are included in U.S. Pat. No. 6,514,767, entitled "Surface Enhanced Spectroscopy-Active Composite Nanoparticles;" U.S. Pat. No. 7,192,778, entitled "Surface Enhanced Spectroscopy-Active Composite Nanoparticles;" U.S. Pat. No. 7,443,489, entitled "Surface Enhanced Spectroscopy-Active Composite Nanoparticles;" and U.S. Published Patent Application No. US 2006-0054506, entitled "Surface Enhanced Spectrometry-Active Composite Nanoparticles;" each of which patents and publications is incorporated herein by reference for all matters disclosed therein.

Although the embodiments disclosed herein are described in terms of SERS nanotags prepared from single nanoparticle cores, it is to be understood that nanoparticle core clusters or aggregates may be used in the preparation of SERS nanotags. Methods for the preparation of clusters of aggregates of metal colloids are known to those skilled in the art. The use of sandwich-type particles as described in U.S. Pat. No. 6,861,263 entitled "Surface Enhanced Spectroscopy-Active Sandwich Nanoparticles" is also contemplated, which patent is incorporated herein by reference for all matters disclosed therein.

The nanoparticle core may be of any material known to be Raman-enhancing, via plasmonic (electromagnetic) factors, chemical factors or a combination of factors. The nanoparticle cores may be isotropic or anisotropic. Nanoparticles suitable to be the core of a SERS nanotag include colloidal metal, hollow or filled nanobars, magnetic, paramagnetic, conductive or insulating nanoparticles, synthetic particles, hydrogels (colloids or bars), and the like. The nanoparticles can exist as single nanoparticles, or as clusters or aggregates of the nanoparticles.

Nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. Another class of nanoparticles that has been described includes those with internal surface area. These include hollow particles and porous or semi-porous particles. While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle. A nanoparticle as defined herein also includes a nanoparticle in which the metal portion includes an additional component, such as in a core-shell particle.

Each SERS nanotag is typically encoded with one or multiple unique reporters, comprising an organic or inorganic molecule or an organic or inorganic material at the interface between the nanoparticle core and shell of glass or other suitable encapsulant. This approach to detection tags leverages the strengths of Raman scattering as a high-resolution molecular spectroscopy tool and the enhancements associated with SERS, while bypassing the shortcomings often encountered when making stand-alone SERS substrates such as difficult reproducibility and lack of selectivity. SERS nanotags exhibit intense spectra (enhancement factors in excess of $10^6$) at 633 nm, 785 nm, 1064 nm or other suitable excitation wavelengths, which wavelengths can be selected to avoid intrinsic background fluorescence in biological samples such as whole blood and in matrices like glass and plastic.

The encapsulant, which is essentially SERS-inactive or relatively weakly SERS-active, stabilizes the particles against aggregation, prevents the reporter from diffusing away, prevents competitive adsorption of unwanted species, and provides an exceptionally well-established surface. Glass, silica, silicates or other silicon-containing species are well suited as encapsulants.

Typical SERS nanotags do not exhibit wavelength dependent response. Thus, known tags will return an identifiable spectrum when excited at one of several excitation wavelengths. For example, a known tag might be excitable and return a detectable SERS spectrum at both 785 nm and 1064 nm excitation wavelengths. A wavelength selective tag would be useful for many purposes, including but not limited to covert marking of materials or documents. As used herein, a wavelength selective particle is one which cannot be effectively excited or interrogated at one or more wavelengths where the selected reporter molecule/metal nanoparticle combination would normally produce a SERS spectrum.

For example, a wavelength selective SERS nanotag might be SERS active when using a 1064 nm excitation wavelength but inactive at 785 nm, where activity at 785 nm would be expected based upon the reporter. It is important to note that many of the examples discussed herein feature tags which would not be SERS-active at 785 nm, but would be easily recognized using 1064 nm excitation. This particular wavelength selectivity is representative only. The disclosed or similar methods might be used to fabricate the reverse tag, showing a spectrum at 785 nm but none at 1064 nm. In addition the methods and materials described may be adaptable to other suitable wavelengths. Moreover, combinations of effects (or materials) can be used to generate more complex wavelength-response profiles. For example, a SERS tag might excitable at 633, 785, and 1064 nm. The particle is then coated with materials that adsorb light strongly at 633 and 1064 nm, but not 785 nm Excitation at either of the former frequencies would not yield a spectrum, but excitation at the latter would. Alternatively, the profile could be reversed so that SERS spectra are obtainable at 633 nm and 1064 nm excitation but not at 785 nm excitation. All permutations of wavelength selectivity are within the scope of this disclosure.

One method of imparting wavelength selectivity to an otherwise non-selective tag is to add a coating to a tag which blocks light that would otherwise cause excitation. For example, the coating of a typical SERS nanotag as described above may be supplemented with Au nanorods that block light at 785 nm, but not at 1064 nm. This method is more fully discussed in Examples 1-5 below.

An similar approach to tuning the wavelength selectivity of a SERS tag in an authentication application is to overcoat a layer of SERS nanotags with a second layer of material that blocks absorption at a given wavelength. For example, if a SERS tag that is responsive to 785 and 1064 nm excitation is placed into a varnish and coated on to a piece of paper, interrogation at either wavelength will yield a SERS spectrum. If, however, a layer of black ink that absorbs strongly at 785 nm but transmits completely at 1064 nm is applied over the SERS tag coating, no SERS spectrum will be seen at 785 nm excitation but a normal spectrum will be seen at 1064 nm excitation.

Another approach is to use a reporter that has non-zero extinction at the excitation wavelength, giving rise to surface enhanced Resonance Raman spectroscopy (SERRS). While it is true that larger absorbances of the reporter molecule at the excitation wavelength give rise to greater resonant enhancements, it is also true that greater absorbances also lead necessarily to increased likelihood of irreversible deactivation processes from the excited state, which could lead to decreased tag stability.

EXAMPLE 1—Au Nanorods Associated with SERS Nanotags

Several physical mixtures of SERS nanotags and Au nanorods were prepared. The UV-visible light extinction and SERS behavior of the mixture at 785 and 1064 nm are plotted in FIG. 1. In particular, the Raman spectra of SERS nanotag/Au nanorod mixtures are illustrated with data acquired at 785 nm (chart 102) and 1064 nm (chart 104). SERS nanotag concentrations were held constant and nanorod concentrations were varied as indicated on charts 102 and 104. UV-visible extinction spectra of the samples are also shown in chart 106 as well as a plot of SERS response versus nanorod concentration in chart 108. A nearly complete suppression of signal at 785 nm may be noted, while the signal at 1064 nm is relatively unaffected. It may also be noted that the sample containing the most nanorods could not be measured by UV-visible because its extinction was too high for the instrument to read.

EXAMPLE 2—Au Nanorods Electrostaticly Associated with SERS Nanotags

While the results obtained in Example 1 demonstrate that the first disclosed method of imparting wavelength selectivity is conceptually sound, the adsorption of an adequate amount of Au nanorods to the nanotags is challenging. Compelling progress has been made toward overcoming the adsorption challenge by using electrostatic methods to bind nanorods to the glass-encapsulated nanotags. Generally the enhanced adsorption technique involves associating a charged coating with the nanorods and an oppositely charged coating with the SERS nanotags. For example, as initially produced, the nanorods used in Example 1 may be stabilized by a positively-charged bilayer of CTAB (cetyltrimethylammonium bromide). However, removal of excess CTAB (which hinders adsorption) can destabilize the rods and cause aggregation. Coating the nanorods with negatively charged polymers, allows more complete cleaning. To fully implement this method, the SERS nanotags must be coated with a positively charged polymer, as well.

Figure 2:
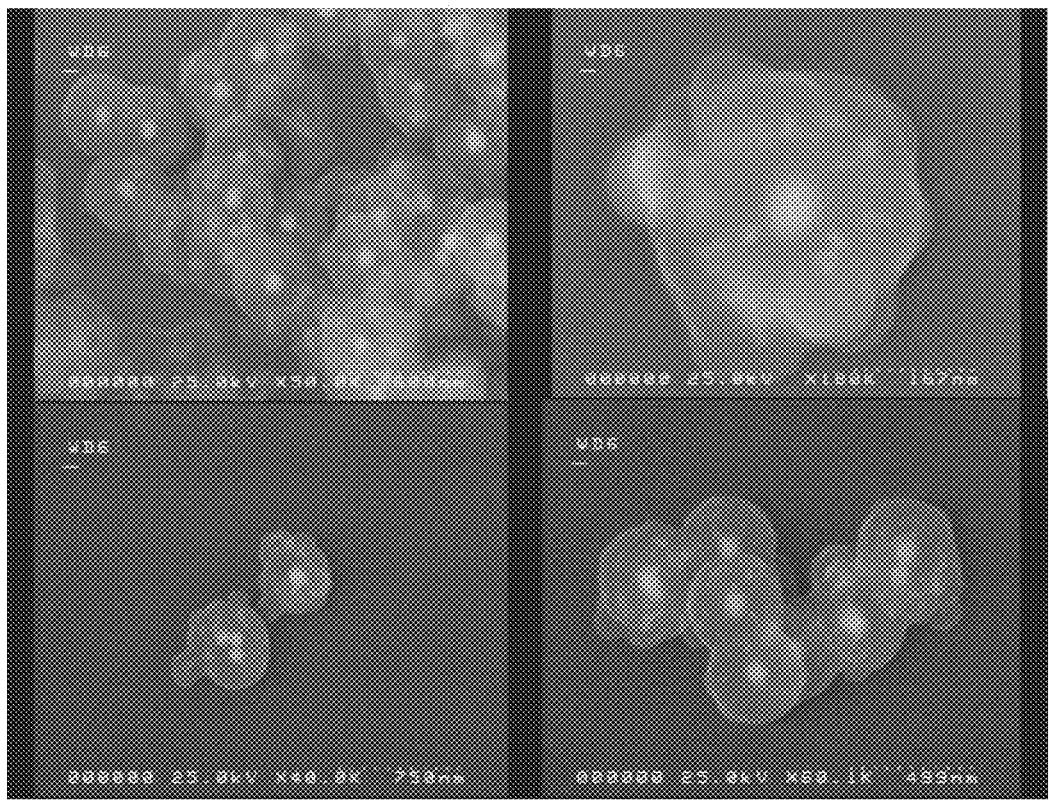
FIG. 2 is a composite of multiple TEM images of the particles of Example 2 featuring Au nanorods electrostaticly associated with SERS nanotags.
Figure 3:
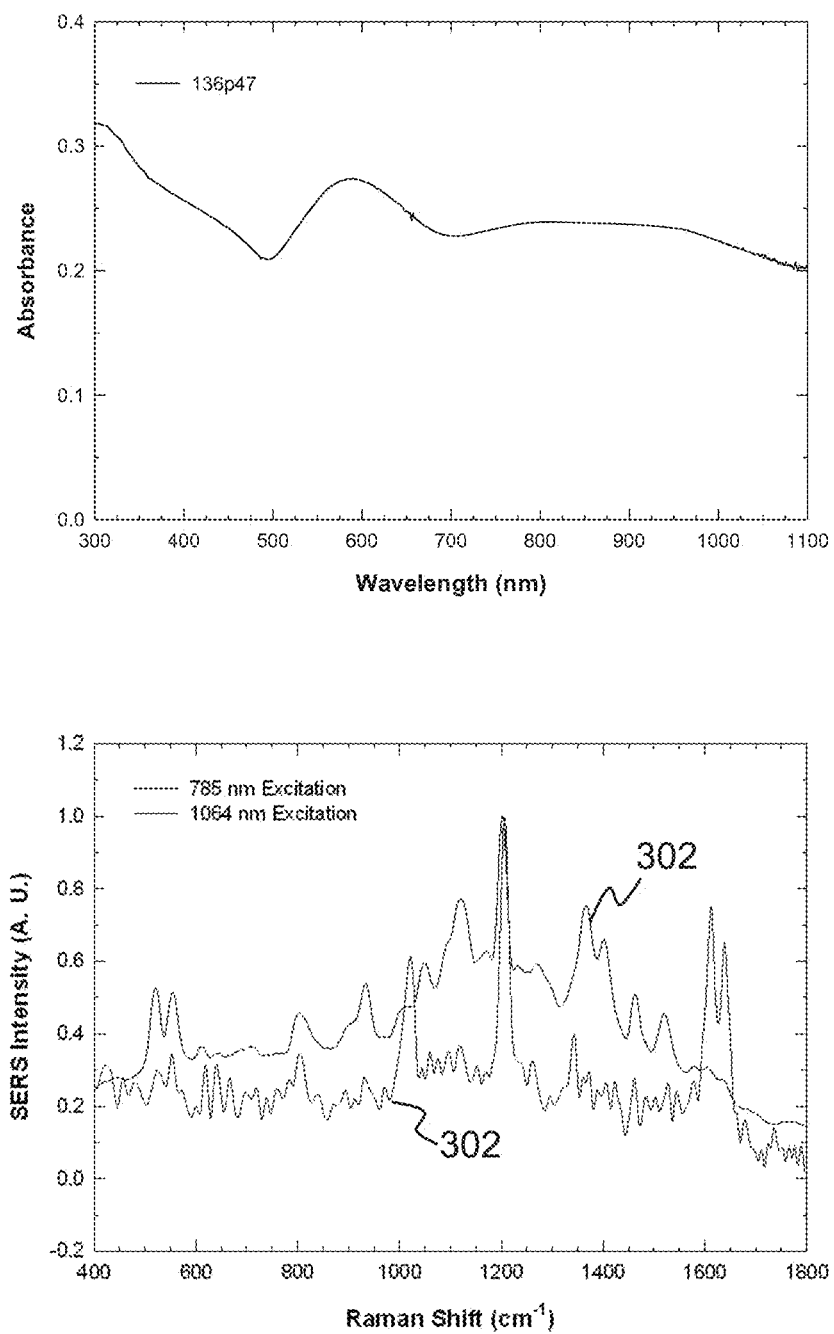
FIG. 3 is a graphic representation of UV-visible light extinction characteristics and normalized SERS responses at selected wavelengths of the particles of Example 2.

In addition, electrostatic combination methods may be enhanced by association of the nanorods with another molecule. In Example 2, the nanorods were mixed with a small amount of a resonant SERS reporter, identified as SERS-817. Subsequently, the nanorods were stabilized by a negatively charged polymer and cleaned extensively. A physical mixture was prepared with SERS nanotags that had previously been coated with a positively charged polymer, promoting some adsorption of rods to SERS particles. After a sufficient incubation period, the mixture was stabilized by addition of an excess of negatively charged polymer ('encapsulating' the nanotag/nanorod assemblies and allowing them to be more easily cleaned). The assemblies were briefly cleaned to remove the majority of unbound nanorods and excess polymers, after which they were encapsulated in glass. The resulting particle assemblies are shown in the TEM images of FIG. 2. The particles are observed to be quite clumpy and do not exhibit a particularly strong SERS signal at 1064 nm. As shown in FIG. 3, these particles do however have distinct and unique signatures at 785 (graph trace 302) and 1064 nm (graph trace 304), with the 1064 nm signature corresponding to the BPE reporter on the SERS nanotags and with the 785 spectrum corresponding to the SERS spectrum of the reporter SERS-817 which was added to the nanorods in an initial step. Thus, this result, as illustrated in FIG. 3 demonstrates that at 785 nm, photons are not reaching the inner core or inner reporter molecule. If 785 nm excitation light were reaching the core of the SERS nanotags, an intense spectrum of the BPE reporter would be present.

EXAMPLE 3—Au Nanorods as Plasmon Absorbers

Figure 4:
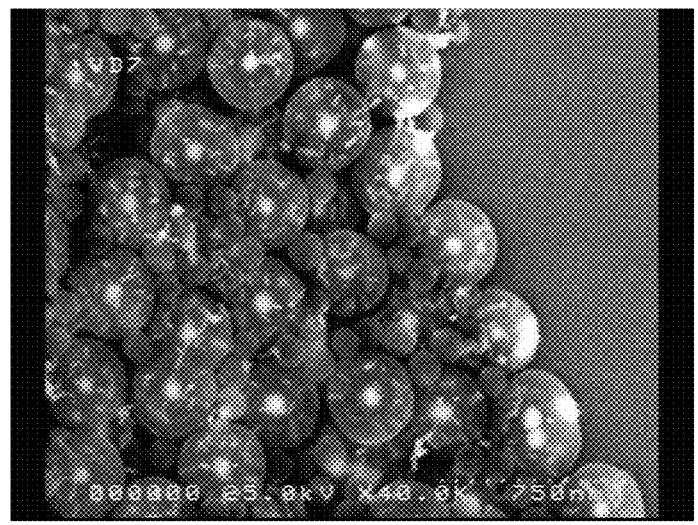
FIG. 4 is a composite of multiple SEM images of the particles of Example 3.
Figure 4:
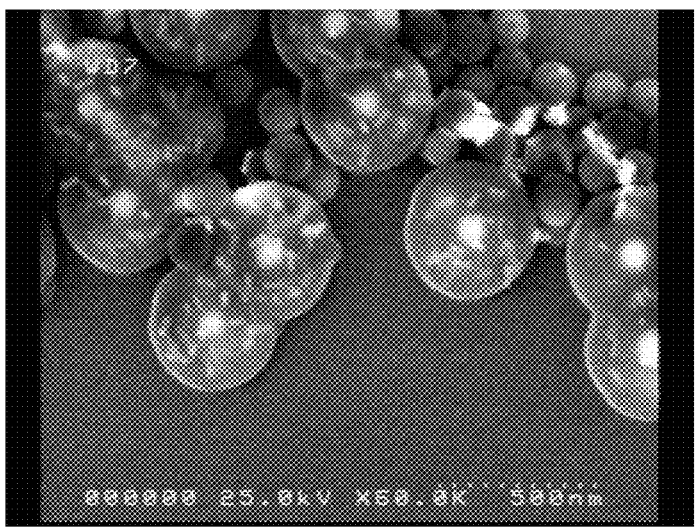
Figure 5:
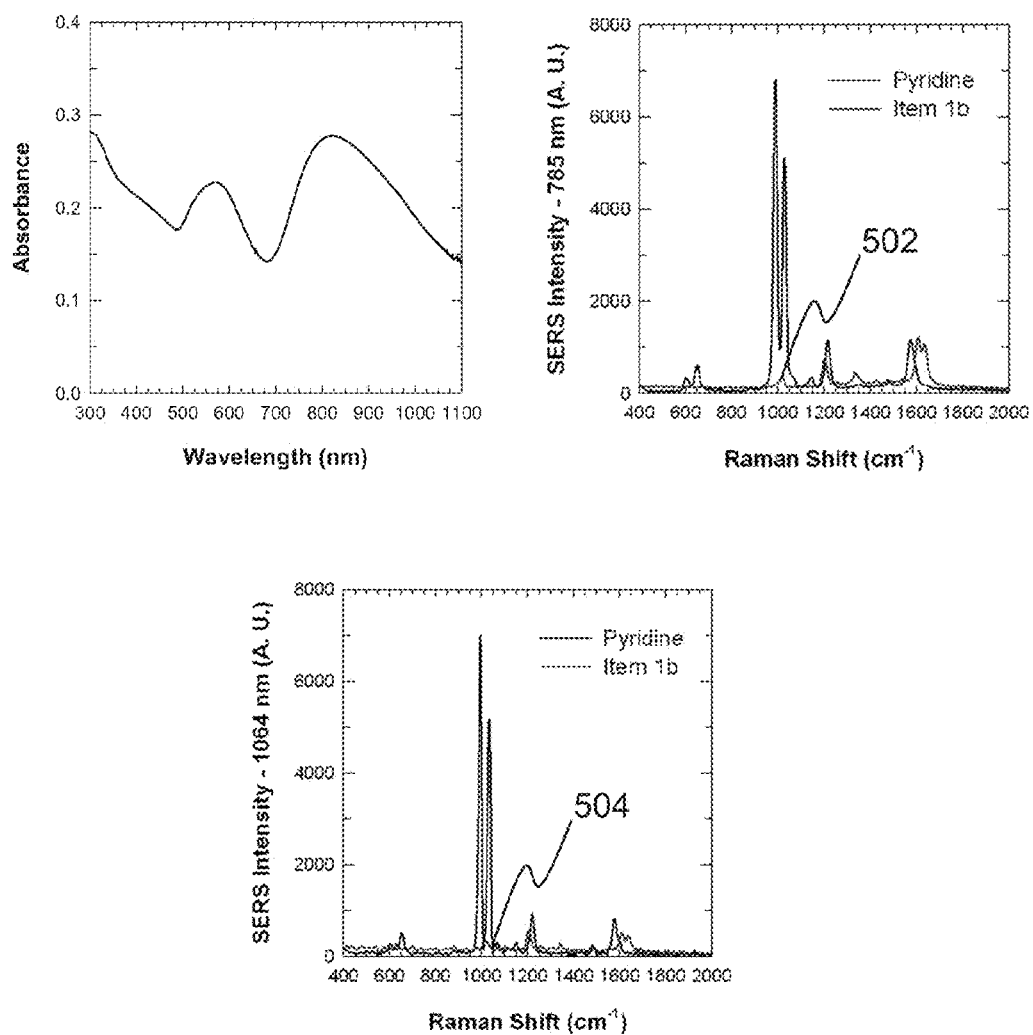
FIG. 5 is a graphic representation of UV-visible light extinction characteristics and SERS activity at selected wavelengths for the particles of Example 3.

The adsorption characteristics of nanorods associated with SERS nanotags may be improved to enhance the wavelength selectivity of the resulting particles. The TEM images of FIG. 4 are of a nanotag sample that was coated with nanorods (via electrostatic adsorption, as previously described). This sample however, utilized nanorods that because of the nanorod shape, size or aspect ratio are inherently better suited to blocking 785 nm excitation energy. Accordingly, as shown in FIG. 5, the SERS nanotags of Example 3 display significantly lower SERS response at 785 nm than the original tags (See graph trace 502). All data in FIG. 5 was acquired at a gold concentration of 12.5 µg/mL. The observed reduction in signal is about ten times less than the unmodified tags. However, the nanorod extinction appears to have broadened, likely due to aggregation, causing the signal at 1064 nm to be significantly impacted (graph trace 504). This result is further evidence that plasmon absorbers can be effectively used to dampen the SERS response at a given wavelength, and thus create wavelength selective particles.

EXAMPLE 4—Glass-Coated Au Nanorods as Plasmon Absorbers

Figure 6:
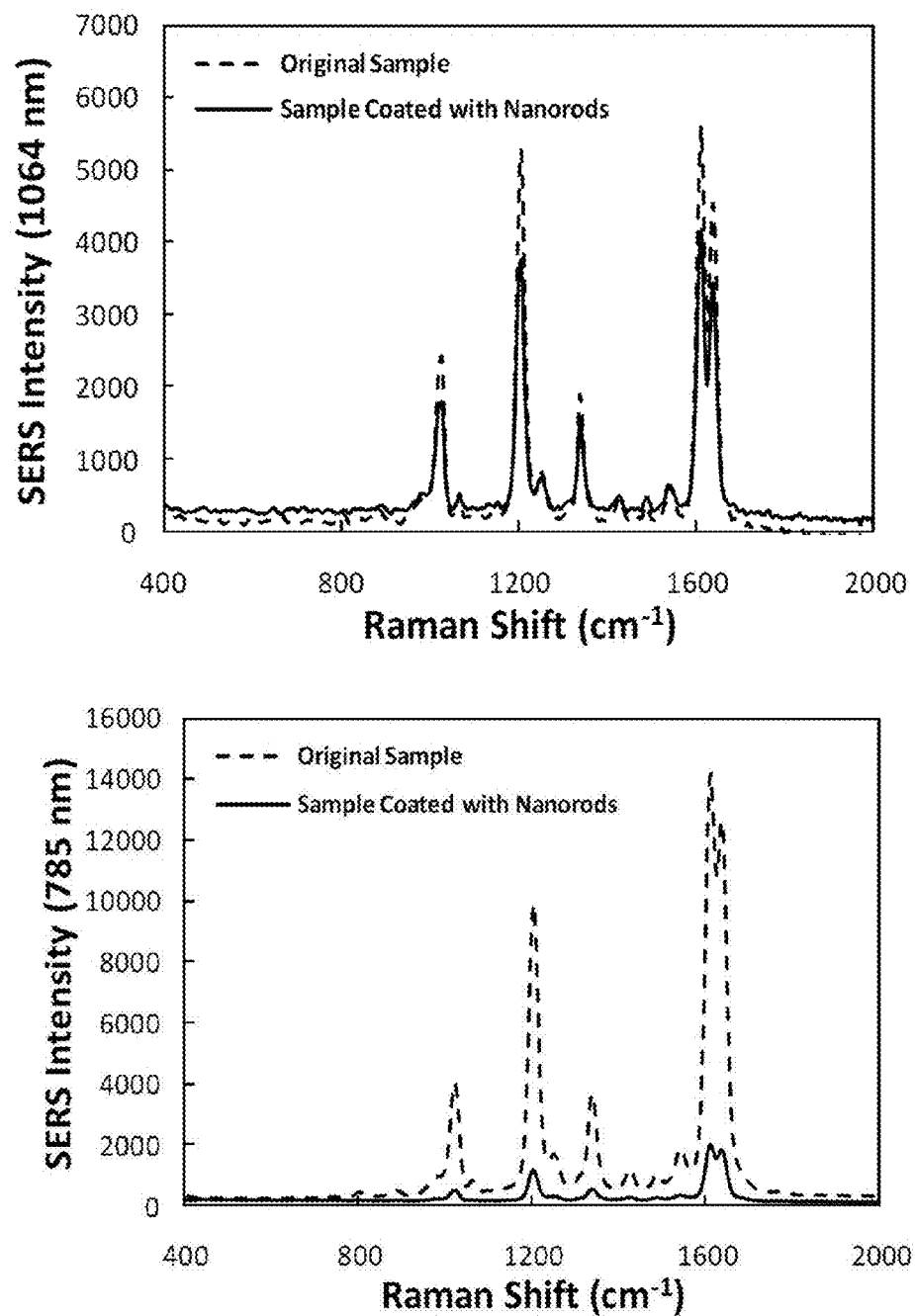
FIG. 6 is a graphic representation of the SERS activity of the particles of Example 4.
Figure 7:
FIG. 7 is a SEM image of the particles of Example 4.

The plasmonic properties of nanorods associated with the SERS nanotags may be stabilized prior to association with the SERS nanotags to prevent changes in the plasmonic properties caused by nanorod-nanorod interactions. In this example, gold nanorods were first coated with a thin glass shell. This glass shell prevents plasmonic changes caused by aggregation or coalescence of the nanorods before or during their adsorption to the SERS nanotags. Thus, the optical properties of the gold nanorods are preserved and a much more specific wavelength response is observed. As previously described, the glass-coated nanorods can then be readily adsorbed directly to the SERS nanotags using electrostatic methods. FIG. 6 shows Raman spectra of SERS nanotags before and after treatment with silica-coated nanorods. The SERS intensity at 785 nm versus 1064 nm is reduced by approximately 8-fold after the treatment. FIG. 7 shows an SEM of the nanorod-nanotag composite particles.

EXAMPLE 5—Plasmonic Shells as Plasmon Absorbers

Figure 8:
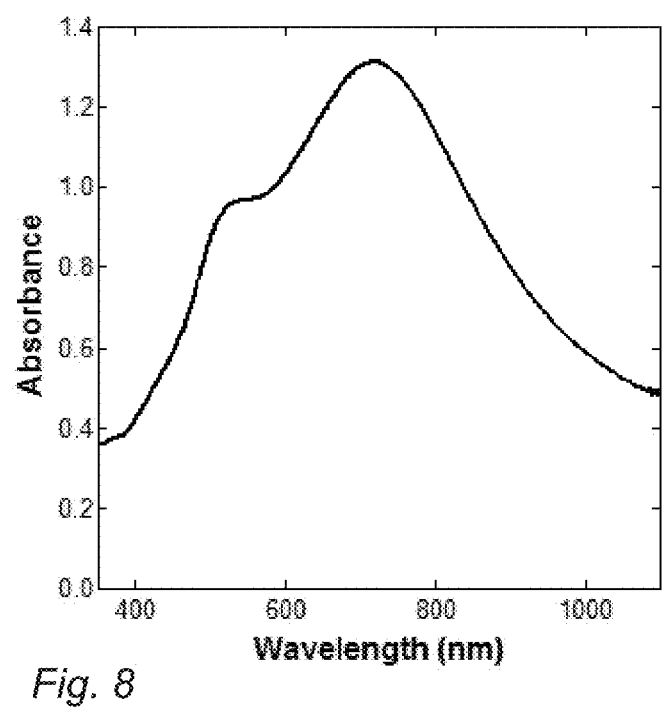
FIG. 8 is a graphic representation of SERS activity of the particles of Example 5.

Core-shell structures with dielectric cores surrounded by nanoscale metallic shells can be engineered to have plasmon resonances in the near-IR. See for example the Absorbance spectrum of a silica-AG core shell particle of FIG. 8. In particular, the relative dimensions of the core and shell can be designed to yield a plasmon resonance around 785 nm. Such a structure would attenuate the SERS response of a SERS nanotag embedded within the structure since the plasmon resonance of the shell would prevent light from the excitation laser to reach the nanotag, and also prevent Raman scattered light from escaping. Since the plasmon resonance can be designed to absorb minimally at 1064 nm, the particle geometry can be adjusted to minimally impact the SERS signal of the nanotag at 1064 nm.

Alternative Methods of Creating Wavelength-Selective SERS Particles

A. Molecular Absorbers

Molecular absorbers may be utilized to block a selected wavelength, for example either the 785 nm (or other wavelength) excitation source, or the resultant SERS emission. However, the cross section of typical chemical absorbers will be much smaller than that of Au nanorods, thus requiring significantly more of the molecule to be present. This may, however, be advantageous as many of these molecular absorbers exhibit weak fluorescence. At high concentrations, this fluorescence can be quenched, resulting in a particle with minimal, featureless emission.

One method that may provide for high doping levels is to create a porous glass shell that has a very high surface area. If near IR absorbers can be physically adsorbed to the glass, the entire particle could be capped with an additional silica layer. The presence of surfactants in the glass growth process can lead to mesoporous coatings, with very high surface areas. Moreover, pseudomorphic transformation methods may allow already prepared SERS nanotags to be converted into tags with mesoporous shells. The pores may then, optionally, be capped to prevent the escape of the dye or blocking molecule.

Alternatively, an absorber can be covalently linked to the silica surface of a SERS Nanotag via a silane reagent such as 3-aminopropytrimethoxysilane (APTMS) or any other coupling agent. In this manner, the molecules can be incorporated throughout the silica as thicker glass shells are formed.

Any materials that absorb light at a wavelength of interest can potentially be used for a molecular absorber application. For example, tags may be incorporation into an ink that absorbs at the desired wavelength.

EXAMPLE 6—SERS Nanotags Surrounded by Molecular Absorbers

Figure 9:
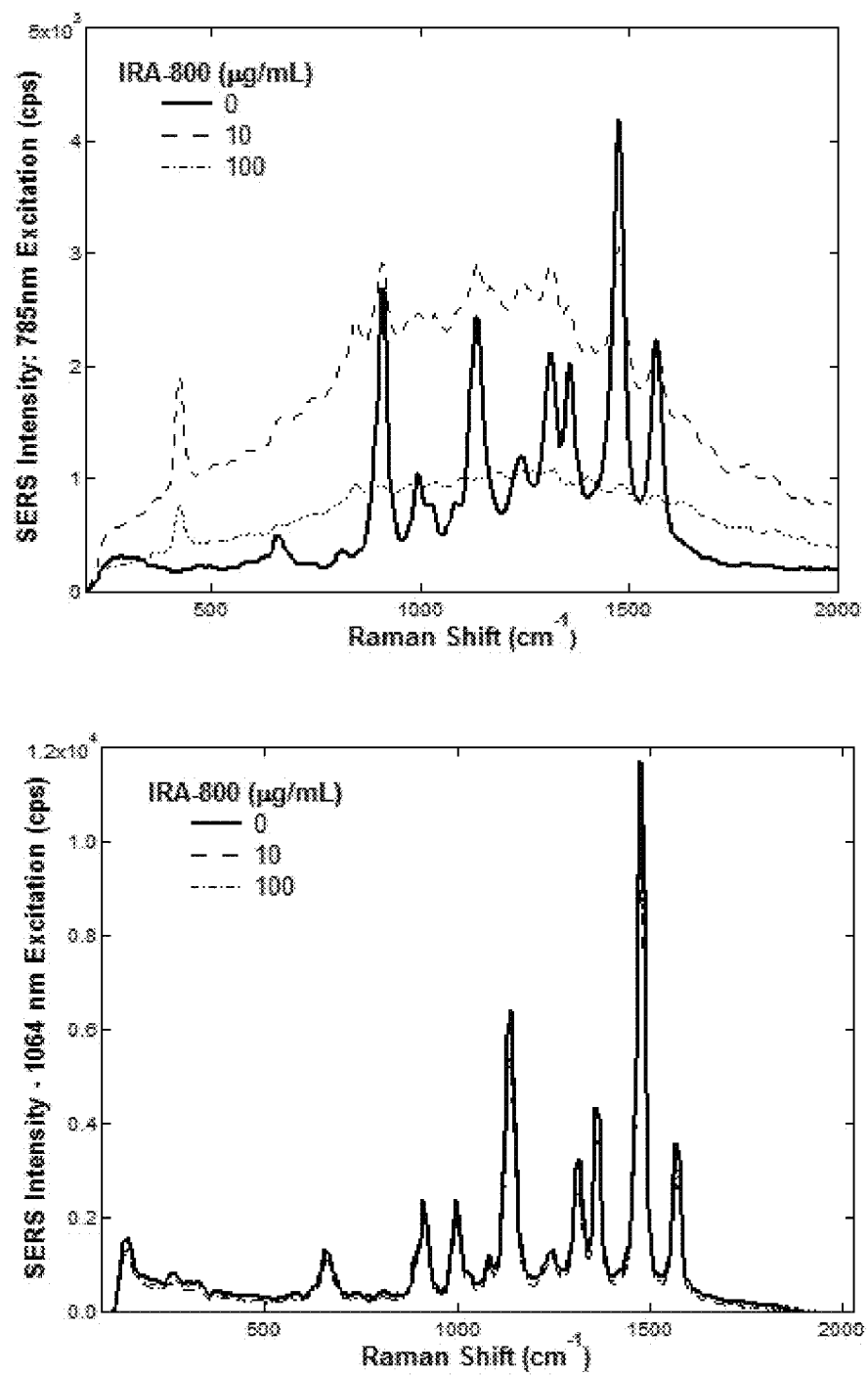
FIG. 9 is a graphic representation of SERS activity at selected wavelengths for the particles of Example 6.

The data represented in FIG. 9 demonstrates that molecular absorbers can be used to mask the signal from a SERS Nanotag using 785 nm excitation, while leaving the signal from 1064 nm excitation unaltered. For Example 6, SERS Nanotags were suspended in aqueous solutions containing no molecular absorber, and 10 and 100 µg/mL of a molecular absorber identified as IRA-800. The concentration of SERS Nanotags was the same in all cases. At 10 µg/mL of the molecular absorber, the SERS signal at 785 nm from the SERS Nanotag is not readily apparent, although weak fluorescence from the molecular absorber is observed. However, at an absorber concentration of 100 µg/mL, not only is the SERS signal completely masked, the fluorescence from the molecular absorber is also quenched, resulting in weak, featureless emission at 785. In contrast, the SERS response at 1064 nm is virtually unchanged in these solutions.

EXAMPLE 7—SERS Nanotags with Mesoporous Encapsulant

Figure 10:
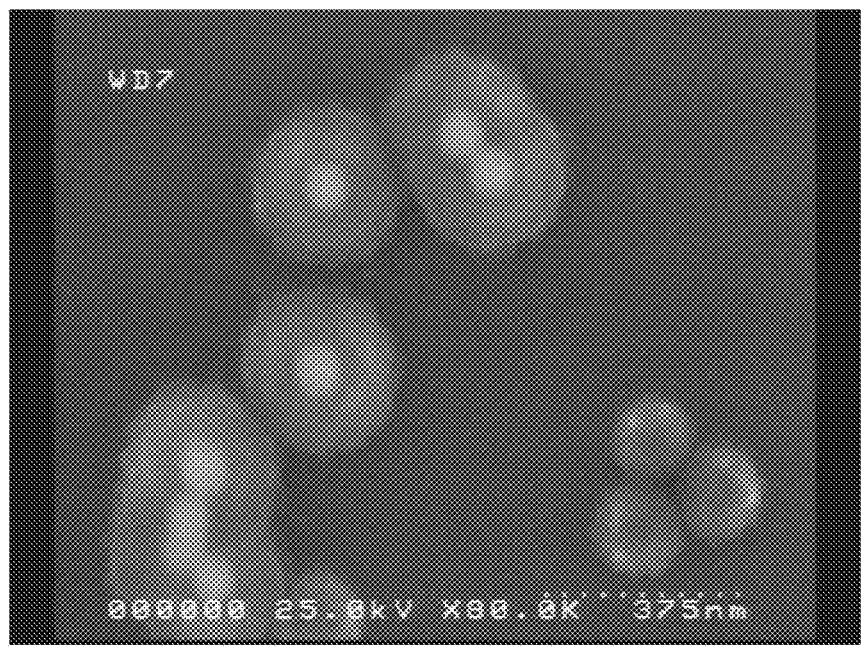
FIG. 10 is an SEM image of SERS nanotags featuring a mesoporous silica encapsulant as described in Example 7.

The particles of Example 7 feature an additional glass coating done in the presence of a surfactant, CTAB, to prepare a mesoporous encapsulant as described above. Although it is difficult to determine if the glass is truly porous, as shown in FIG. 10 the coating definitely appears different than the smooth coatings that are obtained from typical SERS nanotag encapsulating processes. These pores are expected to be <5 nm in size.

B. Tuning of Surface Plasmon

An alternative method to impart wavelength selectivity to a SERS nanotag is to produce enhancing tags with inherently better response at 1064 nm than at 785 nm (for example). This tuning may be accomplished by judicious choice of tag material, shape, size or degree of aggregation.

C. Use of Resonant Reporters

Molecules with absorption features near 1064 nm can provide resonance enhancement. For example the dye IR-1048 (sigma-aldrich) has strong molecular absorption centered at 1048 nm while the dye IR-27 has a maximum absorbance at 988 nm.

D. Charge-Transfer Resonance

Other classes of molecules that give enhanced response at 1064 nm versus other wavelengths include azopyridine, various AZP/benzocinnoline (specifically molecules better at 1064 nm than 785 nm), Fluorophores/metal complexes, Photochromic/thermochromic molecules (spiropyrans) and others.

E. Masking SERS Signal

Certain examples detailed above impart wavelength selectivity to a SERS nanotag by blocking the incidence of an excitation wavelength or blocking the emission of a SERS spectrum caused by excitation at the selected wavelength. Alternatively, the SERS signal of a SERS nanotag may be generated, but effectively masked prior to detection. For example, a molecule or material may be associated with an encapsulant which is strongly fluorescent using 785 nm excitation. SERS detection may then occur with 1064 nm excitation.

EXAMPLE 8—SERS Signal Masked by Dluorescence

Figure 11:
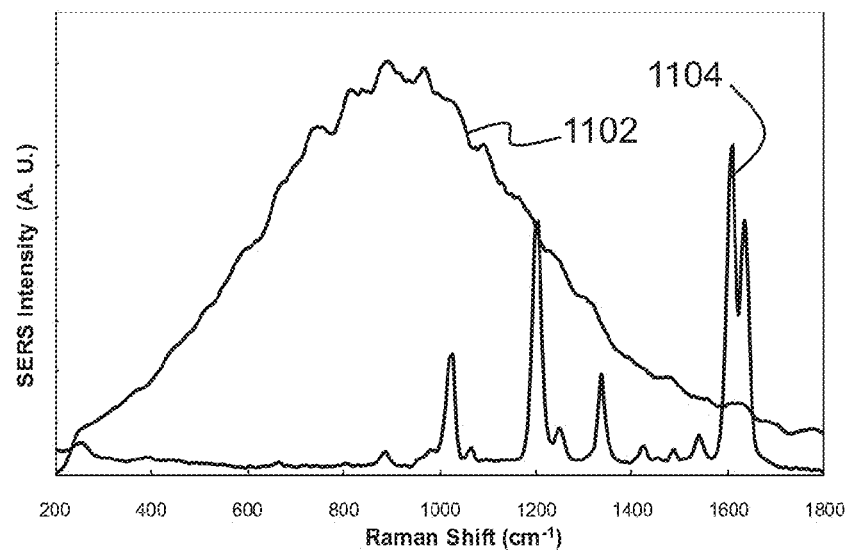
FIG. 11 is a graphic representation of the Ramen spectra at selected wavelengths of SERS nanotags after mixture with a fluorescent masking agent as Described in Example 8.

FIG. 11 shows two spectra obtained from a mixture containing the dye IR-140 (100 nM) and a sample of SERS tags. When excited at 785 nm a strong fluorescence emission spectrum 1102 is observed due to IR-140 and the presence of the SERS tag cannot be detected. The fluorescence effectively masks the fact that a Raman label is present. When excited at 1064 nm the Raman spectrum from the SERS tag 1104 is detected. This result was obtained by physical mixing of the two substances. Alternatively, a fluorescent material could be incorporated into the structure of the SERS tag.

Note that the SERS at 785 nm is completely obscured by fluorescence, but there is no fluorescence when excited at 1064 nm. The amount of dye added to the particles corresponds to much less than monolayer coverage, implying that very few fluorophores would need to be incorporated into the SERS tag for an effective wavelength selective tag.

F. Alternative Read-Out Methods

Alternate read-out methods may be used to impart wavelength selectivity to SERS nanotags. Typically Raman scattering occurs on the picosecond time scale while fluorescence occurs at the fastest occurs in the nanosecond regime and other luminescent processes can be much slower. Because of this difference in temporal behavior it is possible to detect Raman scattering even when luminescence is occurring at the same wavelengths. Time resolved detection can be used by exciting both Raman scattering and luminescence with pulses of light which are much shorter than the luminescent lifetime. Time-gated detection can then be used to measure the Raman scattering while rejecting most of the luminescence. Alternatively, in the frequency domain, the amplitude of the excitation source may be modulated at high frequency. In this fashion, processes with rapid response (i.e. Raman scattering) follow the modulation frequency and can be detected with a frequency and phase sensitive detector. The signal from processes with slower response may be rejected by the frequency sensitive detector. Thus, material that possesses both spectrally unresolved fluorescence and Raman scattering may be used as a Raman tag.

G. Transient photobleaching

It is possible to use strong pulses of light which cause the absorption of a molecule to saturate. This happens when the rate at which photons are absorbed exceeds the rate at which the excited state can be depopulated. At that point the incoming photons would be free to excite Raman scattering and SERS. An appropriate readout system would require a pulsed light source and fast detection systems.

Alternative embodiments include methods of manufacturing a wavelength selective SERS nanotag as described above.

Alternative methods also include using a wavelength selective SERS nanotag to mark or tag an item, substance, document or article, such that the tag may be detected at fewer interrogation frequencies than would be expected based upon the nature of the reporter molecule used with the SERS nanotag. The tagging methods comprise providing a SERS active particle as described above and associating the particle with a material or object of interest. The method of tagging may further include obtaining a SERS spectrum and other identification information from the particle in association with the material of interest and thereby identifying the marked object or substance. Supplemental identification information can be associated with the tag or the object, as described herein.

The small, robust, non-toxic, and easily-attachable nature of the particles disclosed herein allows their use for tagging virtually any desired object. The tagged object can be made of solid, liquid, or gas phase material or any combination of phases. The material can be a discrete solid object, such as a container, pill, or piece of jewelry, or a continuous or granular material, such as paint, ink, fuel, or extended piece of, e.g., textile, paper, or plastic, in which case the particles are typically distributed throughout the material.

Examples of specific materials or objects that can be tagged with the particles disclosed herein, or into which the particles can be incorporated include, but are not limited to:
Packaging, including adhesives, paper, plastics, labels, and seals
Agrochemicals, seeds, and crops
Artwork
Computer chips
Cosmetics and perfumes
Compact disks (CDs), digital video disks (DVDs), and videotapes
Documents, money, and other paper products (e.g., labels, passports, stock certificates)
Inks, paints, varnishes, lacquers, overcoats, topcoats, and dyes
Electronic devices
Explosives and weapons
Food and beverages, tobacco
Textiles, clothing, footwear, designer products, and apparel labels
Polymers
Insects, birds, reptiles, and mammals
Powders
Luxury goods
Other anti-counterfeiting substances or materials, such as holograms, optically variable devices, color-shifting inks, threads, and optically-active particles
Hazardous waste
Movie props and memorabilia, sports memorabilia and apparel
Manufacturing parts, automobile parts, aircraft parts, truck parts
Petroleum, fuel, lubricants, gasoline, crude oil, diesel fuel, fuel additive packages, crude oil
Pharmaceuticals, prescription drugs, over-the-counter medicines, and vaccines The particles disclosed herein can be associated with the material in any way that maintains their association, at least until the particles are read. Depending upon the material to be tagged, the particles can be incorporated during production or associated with a finished product. Because they are so small, the particles are unlikely to have a detrimental effect on either the manufacturing process or the finished product. The particles can be associated with or attached to the material via any chemical or physical means that does not inherently interfere with particle functionality. For example, particles can be mixed with and distributed throughout a liquid-based substance such as paint, oil, or ink and then applied to a surface. They can be wound within fibers of a textile, paper, or other fibrous or woven product, or trapped between layers of a multi-layer label. The particles can be incorporated during production of a polymeric or slurried material and bound during polymerization or drying of the material. Additionally, the surfaces of the particles can be chemically derivatized with functional groups of any desired characteristic, for covalent or non-covalent attachment to the material. When the particles are applied to a finished product, they can be applied manually by, e.g., a pipette, or automatically by a pipette, spray nozzle, or the like. Particles can be applied in solution in a suitable solvent (e.g., ethanol), which then evaporates.

The particles disclosed herein have a number of inherent properties that are advantageous for tagging, tracking and identifying applications. They offer a very large number of possible codes. For example, if a panel of particles is constructed with 20 distinguishable Raman spectra, and an object is labeled with two particles, there are 20*19/2=190 different codes. If the number of particles per object is increased to 5, there are 15,504 possible codes. Ten particles per object yields $1.1 \times 10^6$ different codes. A more sophisticated monochromator increases the number of distinguishable spectra to, e.g., 50, greatly increasing the number of possible codes. Alternatively, different amounts of particles can be used to generate an exponentially-increased number of possible codes. For example, with just four different particle types (N=4), present at three different intensity levels (e.g. High, Medium, Low) (L=3), chosen three at a time (P=3), can generate 58 different codes. With N=10, P=3, L=1, the number of codes is 175. With N=50, P=5, L=4, over a billion codes are possible.

In some embodiments, the particles may be applied to a document or other item in an ink or other marking material. Inks include, but are not limited to flexographic ink, lithographic ink, silkscreen ink, gravure ink, bleeding ink, coin reactive ink, erasable ink, pen reactive ink, heat reactive ink, visible infrared ink, optically variable ink, and penetrating ink. photochromic ink, solvent/chemical reactive ink, thermochromic ink, and water fugitive ink. A particle may also be applied in electrophotographic and ink jet printing machines and other systems including offset lithography, letterpress, gravure, heliogravure, xerography, photography, silk-screening systems, systems for imagewise deposition of discrete quantities of a marking material on a substrate surface, such as paint, chemical, and film deposition systems; and systems for integration of colorant materials in an exposed surface of a fibrous substrate, such as textile printing systems.

It should be noted that additional security features may be included or utilized along with the disclosed tags for a particular item or documents. One such additional security feature may be a separate security ink, such as bleeding ink, coin reactive ink, erasable ink, pen reactive ink, heat reactive ink, visible infrared ink, optically variable ink, penetrating ink. photochromic ink, solvent/chemical reactive ink, thermochromic ink or water fugitive ink. The tags may be applied as part of the ink, or in a separate step. Other non-ink based security features which may be utilized in addition to the disclosed tags for document or item marking include the use of an ascending serial number (horizontal and/or vertical format), bar code and numerals, colored fibers, embedded security thread, face-back optical registration design (transparent register), foil imprints, holograms, latent impressions, micro printing, optical variable devices (OVD), planchettes, raised marks, segmented security threads, and watermarks.

The disclosed particles may be applied by coating an image, including but not limited to a hologram image, made with toner or ink compositions known in the art, as with an overcoat varnish, or a starch overcoat.

In the case of documents with other security features, such as those including polymer threads or metal foils, the particles may be applied to additional feature, such as the thread or the foil. Single tags may be considered to represent a bit of data that may be changeable according to the methods described herein. Thus groups of distinguishable particles disclosed herein may be applied to constitute an "alphabet" and combined as words or encoded information, which may be selectively variable, or variable over time.

The particles disclosed herein can be identified using a conventional spectrometer, for example a Raman spectrometer. In fact, one benefit of using SERS particles is the versatility of excitation sources and detection instrumentation that can be employed for Raman spectroscopy. Visible or near-IR lasers of varying sizes and configurations can be used to generate Raman spectra. Portable, handheld, and briefcase-sized instruments are commonplace. At the same time, more sophisticated monochromators with greater spectral resolving power allow an increase in the number of unique taggants that can be employed within a given spectral region. For example, the capability to distinguish between two Raman peaks whose maxima differ by only 3 $cm^{-1}$ is routine.

Typically, if a suitable waveguide (e.g., optical fiber) is provided for transmitting light to and from the object, the excitation source and detector can be physically remote from the object being verified. This allows the disclosed particles to be used in locations in which it is difficult to place conventional light sources or detectors. The nature of Raman scattering and laser-based monochromatic excitation is such that it is not necessary to place the excitation source in close proximity to the Raman-active species. Moreover, the particles disclosed herein are amenable for use with all known forms of Raman spectrometers, including some more recent implementations, including spatially offset Raman, Raman absorption spectrometers, instruments to measure Raman optical activity, and so forth.

Another characteristic of the disclosed particles is that the measurement of their spectra does not need to be strictly confined to "line of sight" detection, as with, e.g., fluorescent tags. Thus their spectrum can be acquired without removing the particles from the tagged object, provided that the material is partially transparent to both the excitation wavelength and the Raman photon. For example, water has negligible Raman activity and does not absorb visible radiation, allowing the particles disclosed herein in water to be detected. The particles can also be detected when embedded in, e.g., clear plastic, paper, or certain inks.

The disclosed particles also allow for quantitative verification, because the signal intensity is an approximately linear function of the number of analyte molecules. For standardized particles (uniform analyte distribution), the measured signal intensity reflects the number or density of particles. If the particles are added at a known concentration, the measured signal intensity can be used to detect undesired dilution of liquid or granular materials.

In another embodiment, SERS particles in tagged items are detected with an instrument capable of measuring inelastically scattered light and determining the identity of the SERS particles and by extension the tagged item. In one embodiment, the instrument requires an excitation source that illuminates the tagged item. The inelastically scattered light from the SERS particles is collected. The spectrum of scattered light is analyzed and the identity of the particles, and hence the item, is determined. The reader may be a Raman Spectrometer. The instrument to collect and analyze the Raman spectrum (the reader) can be as small as 1 cubic millimeter and as large as 1000 cubic meters.

The light source used to excite the particles may be a monochromatic light from a laser operating in the solid state, in gas or in liquid. The laser can be continuous or pulsed. A continuous laser can have powers from 01. femtowatt up to 1 megawatt. A pulsed laser can have similar total power with pulses as short as less than 1 femtosecond, and with a pulse repetition rate up to 1 terahertz. Alternatively, multiple light sources can be used. In one embodiment, multiple separate excitation wavelengths are used to determine the presence or absence of wavelength selective particles as described above or to compensate for detectors that have low photon-to-electron conversion efficiencies in certain spectral regions, using one excitation wavelength to cover a certain portion of the Raman shift window (e.g. 100-1800 $cm^{-1}$), and the second to cover another (e.g. 1801-3600 $cm^{-1}$).

In addition to lasers, the light can come from an electroluminescent material such as a light emitting diode. Alternatively, the excitation light can come from an incandescent or fluorescent light source. In all embodiments the excitation wavelength range can be from 100 nm to 100 microns. The excitation light can be spectrally filtered with discrete filters or spatially dispersing elements.

In one embodiment, the monochromatic light spectral width is less than 0.5 nm. In other embodiments, the spectral width is from 0.01 nm bandwidth to 100 nm bandwidth. The excitation and collected light may be steered to and from the item under interrogation with lenses, mirrors, light pipes, gratings, waveguides, optical fiber or any other component. All optical and mechanical elements can, but need not be, integrated into a single platform.

In one embodiment the excitation source and collection system are connected to the sample delivery optics with light pipes or optical fibers. In other embodiments, discrete optical elements connect the excitation source and detection element. The discrete optics include lenses, mirrors or other waveguides. In other embodiments the excitation source, the collection spectrometer or all items are made using micro-manufacturing techniques such as LIGA, molding, etching, MEMS, NEMS, lithography, photolithography, or other monolithic methods. The illuminated spot from the excitation source may be larger than 100 microns in diameter. In other embodiments, the illuminated spot may be as small as 100 square nanometers and as large as 1 square meter.

In one embodiment the collected light is analyzed by a spectrometer. The spectrometer uses a grating to disperse the collected light onto an area array detector, preferably a Charge Coupled Device (CCD). The CCD divides the spectrum into bins, with each bin corresponding to a given wavelength range. The number of bins used can range from 1 bin to many thousands of bins. In one embodiment, the number of bins is more than 20.

The optics of the spectrometer typically has a specific spectral resolution. For example, the resolution may be less than 10 nm or between 1 nm to 4 nm. In other embodiments, the resolution is from 0.01 nm to 5000 nm. The selected resolution can be 0.01 $cm^{-1}$ to 40000 $cm^{-1}$ expressed as wave numbers.

In one embodiment, the method of optically separating light into bins uses any form of light dispersion with a prism, grating or any spatially dispersing element. In other embodiments, a digital micro mirror array is used to spatially disperse light. Other tunable spectral filters are used including acousto-optic tunable filters, electro-optics tunable filters, liquid crystal tunable filters. Any form of scanning spectral analysis can be used as well such as Fourier Transform correlation spectroscopy. In another embodiment, a single detection element or an array of detection elements may is used. The spectrum is analyzed with discrete optical filters or with the other aforementioned spectral filtering methods In one embodiment, the detector element is a CCD or photodiode array made from silicon, InGAs, or any other semiconductor. Recently, detectors made from organic materials (e.g. conducting polymers) and from carbon-based composites have been described. In other embodiments, the detection element is any element that converts electromagnetic energy, i.e. photons into electrons or other electrical energy or thermal energy or sound energy.

The converted electrical energy is analyzed by an electrical circuit. The circuit will typically, if required convert the analog signal from the detector to a digital signal that is stored in or analyzed by a computer. The digital signal can be analyzed to determine the presence of the tag. The digital signal can be a discrete signal level or a stream of signal levels corresponding to a spectrum. In other embodiments, the circuit can use analog logic elements to determine the signal level of the tag and whether the item is tagged or not.

In one embodiment, the acquired spectrum is analyzed by a computer to determine the presence of the SERS particles after accounting for the presence of other materials contributing to the spectrum, i.e other inks, materials soiling etc. For example, the SERS particles with a commercially available Raman Spectrometer, such as the Delta Nu Reporter. The Raman spectrometer may be controlled by a small computer in a phone or other personal data assistant. The small computer may communicate with the Raman Spectrometer over a wireless connection, either blue tooth or wi-fi or other wireless protocol. In this embodiment, the small computer may receive the acquired spectrum from the Raman Spectrometer, analyzes the spectrum and identifies the item.

In another embodiment the reader system is part of another machine. The reader uses a signal from the machine to start detection of the tag and perform classification all in real time. The machine contains a central processor that identifies the tagged item and makes a decision on the item whether it is real or not and or whether the tag is correct. The machine can be one used in the processing, issuing, sorting, counting, screening, tracking, or authentication of banknotes or currency, or for any other industrial security application, and where the tagged items could be pills, bullets, items of clothing, machine parts, software, food, beverages, or any other item to which SERS particles are applied.

In other embodiments, the machine is a currency or stamp or document printing press or inkjet printer or digital printer or any other type of printing instrumentation where the reader is used for process monitoring. In other embodiments, the machine is part of a final packaging or labeling line where the taggants are checked as a final step.

In addition to Raman spectral analysis, the instrumentation or reader can perform other functions. For example, the instrument can measure both elastic and inelastic light scattering. Alternatively, the instrument can acquire an optical image of an item as well as a spectral signature. Likewise, the instrument can measure a fluorescence spectrum in one spectral window and a Raman spectrum in another spectral window.

The spectrum can be analyzed for spectral peaks, widths, heights, and positions, numbers of peaks, ratios of peaks, or combinations thereof. The spectrum can be analyzed by any number of mathematical methods, including but not limited to wavelet analysis, principal component analysis, linear and non-linear regression, or combinations thereof. In addition Fourier transform, Laplace transforms, Hildebrand transforms, Hadamard transforms or any other mathematical method, i.e. first to higher order derivatives, first or higher order integrals or any other analysis, can be used to manipulate the spectral information. All of the above methods can be used to remove any interfering or extraneous or unwanted signals, including but not limited to (a) standard interferences, including but not limited to daylight, impurities, paper, ink, thread, fiber, metal, liquids, solids, solvents, moisture, (b) use-related signals, including that from dirt, stains (e.g. coffee, beer, skin fluids), dust, charcoal, trace drugs (e.g. cocaine), and (c) interfering optical signals, including but not limited to fluorescence, luminescence, absorbance, scattering, phosphorescence, and chemiluminescence.

In one embodiment wavelength selective SERS particles are used on their own or in combinations to make codes. Tag and their combinations are organized in a database which can be correlated to products, lot numbers or other attributes. Libraries of know tag spectra can be used to find the wanted tag spectra. Libraries can include all other compounds, spoofs or any other anticipated material. Backgrounds and other components can be separated using the same methods. Backgrounds and other contaminants can be modeled synthetically by using a polynomial or other mathematical function, rolling circle subtraction and spectral filtering The database information can be stored on the detection device or stored on a remote computer. The remote computer could be part of a cellular phone or other mobile device that is linked to a single or multiple instruments. The remote computer could be a personal computer, laptop, or central computing cloud that communicates with a range of instruments, from 1 to 2 million, over the internet connection or other communication protocol. The instruments and computers can be linked through a wireless network Multiple attributes of the SERS particles can be used to determine the identity of a marked item. These attributes include the amount of material and the quality of the spectrum, the amount of the material relative to another material, the spectra relative to other spectra.

The classification of a code or combination of SERS particles can be performed using statistical methods, such as Bayesian methods. These methods can be used to assign probabilities that the sample contains the code. In other methods a threshold is set for an attribute.

While the aforementioned examples are directed toward wavelength selectivity in SERS tags, those skilled in the art will recognize that incorporation of wavelength selective features can be built into particles designed for other optical detection methods, including but not limited to fluorescence, luminescence, phosphorescence, elastic (Rayleigh) light scattering, upconversion, downconversion, and multi-photon processes. Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments have been particularly shown and described with reference to a number of examples, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

The description has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A material or object associated with a wavelength selective surface enhanced Raman scattering (SERS) nanotag comprising:
   at least one of a material or object; and
   a wavelength selective nanotag associated with the material or object, the wavelength selective nano tag comprising;
   a SERS enhancing core;
   a SERS active reporter molecule associated with the core;
   an encapsulant encapsulating the core and reporter association; and a blocking material associated with the encapsulant,
   wherein the blocking material changes an optical behavior of the wavelength selective nanotag when compared to an identical nanotag without the blocking material, by causing a decrease in a Raman spectrum intensity of the wavelength selective nanotag upon SERS interrogation at a first SERS excitation wavelength, while not causing a decrease in the Raman spectrum intensity of the wavelength selective nanotag upon SERS interrogation at a second SERS excitation wavelength.

2. The material or object associated with a wavelength selective SERS nanotag of claim 1, wherein the material or object comprises at least one of packaging, adhesives, paper, plastic, a label, a seal, an agrochemical, seeds, crops, artwork, a computer chip, cosmetics, perfumes, a compact disk, a digital video disk, a videotape, a document, currency, a paper product, a passport, a stock certificate, an ink, a paint, a varnish, a lacquer, an overcoat, a topcoats, a dye, an electronic device, an explosive, a weapon, food, a beverage, tobacco, a textile, clothing, footwear, apparel labels, a polymer, a powder, a hologram, an optically variable device, a color-shifting ink, threads, hazardous waste, a movie prop, memorabilia, a manufactured part, an automobile part, an aircraft part, petroleum, fuel, a lubricant, gasoline, crude oil, diesel fuel, crude oil, a pharmaceutical, a prescription drug, an over-the-counter medicine and vaccines.

3. The material or object associated with a wavelength selective SERS nanotag of claim 2, wherein the material or object comprises ink.

4. The material or object associated with a wavelength selective SERS nanotag of claim 3, wherein said ink comprises one or more of a silkscreen ink, a gravure ink, a bleeding ink, a coin reactive ink, an erasable ink, a pen reactive ink, a heat reactive ink, a visible infrared ink, an optically variable ink, a penetrating ink, a photochromic ink, a solvent/chemical reactive ink, a thermochromic ink, a flexographic ink, a lithographic and a water fugitive ink.

5. The material or object associated with a wavelength selective SERS nanotag of claim 1, further comprising an additional security feature.

6. The material or object associated with a wavelength selective SERS nanotag of claim 5, wherein the additional security feature comprises one or more of a serial number, a bar code, colored fibers, embedded security thread, a face-back optical registration design, a foil imprint, a hologram, a latent impression, a micro printing, an optical variable device, a planchette, a raised mark, segmented security threads, a watermark, polymer threads and a metal foil.

7. The material or object associated with a wavelength selective SERS nanotag of claim 1, wherein the blocking material of the wavelength selective SERS nanotag comprises a nanorod associated with the encapsulant.

8. The material or object associated with a wavelength selective SERS nanotag of claim 7, wherein the nanorod comprises an Au nanorod.

9. The material or object associated with a wavelength selective SERS nanotag of claim 8, wherein the Au nanorod is electrostatically associated with the encapsulant.

10. The material or object associated with a wavelength selective SERS nanotag of claim 7, wherein the blocking material comprises:
a charged polymer associated with the nanorod; and
an oppositely charged polymer associated with the encapsulant.

11. The material or object associated with a wavelength selective SERS nanotag of claim 1, wherein the encapsulant comprises a mesoporous surface.

12. A material or object associated with a wavelength selective surface enhanced Raman scattering (SERS) nanotag comprising:
at least one of a material or object; and
a wavelength selective nanotag associated with the material or object, the wavelength selective nanotag comprising;
a SERS enhancing core;
a SERS active reporter molecule associated with the core;
an encapsulant encapsulating the core and reporter association; and
a masking material associated with the encapsulant,
wherein the masking material changes an optical behavior of the wavelength selective nanotag when compared to an identical nanotag without the masking material, by masking a Raman spectrum intensity of the wavelength selective nanotag upon SERS interrogation at a first SERS excitation wavelength while not masking the Raman spectrum intensity of the wavelength selective nanotag upon SERS interrogation at a second SERS excitation wavelength.

13. The material or object associated with a wavelength selective SERS nanotag of claim 12, wherein the masking material is a fluorescent dye.

* * * * *